(12) United States Patent
Brugger et al.

(10) Patent No.: US 8,192,387 B2
(45) Date of Patent: Jun. 5, 2012

(54) LAST-CHANCE QUALITY CHECK AND/OR AIR/PATHOGEN FILTER FOR INFUSION SYSTEMS

(75) Inventors: James M. Brugger, Newburyport, MA (US); Jeffrey H. Burbank, Boxford, MA (US)

(73) Assignee: NxStage Medical, Inc., Lawrence, MA (US)

( * ) Notice: Subject to any disclaimer, the term of this patent is extended or adjusted under 35 U.S.C. 154(b) by 512 days.

(21) Appl. No.: 12/040,748

(22) Filed: Feb. 29, 2008

(65) Prior Publication Data
US 2008/0203023 A1    Aug. 28, 2008

Related U.S. Application Data

(62) Division of application No. 10/513,693, filed as application No. PCT/US03/17743 on Jun. 5, 2003, now abandoned.

(60) Provisional application No. 60/438,567, filed on Jan. 7, 2003, provisional application No. 60/386,483, filed on Jun. 6, 2002.

(51) Int. Cl.
*A61M 37/00* (2006.01)
*B01D 11/00* (2006.01)
*B01D 61/00* (2006.01)

(52) U.S. Cl. ........................ 604/6.09; 604/4.01; 210/646

(58) Field of Classification Search .................. 210/646, 210/321.79, 321.8–321.9, 433.1, 500.23, 210/650; 422/44; 604/4.01
See application file for complete search history.

(56) References Cited

U.S. PATENT DOCUMENTS

| | | | |
|---|---|---|---|
| 2,995,334 A | 8/1961 | Henderson et al. | |
| 3,034,085 A * | 5/1962 | Pauler et al. | 439/191 |
| 3,100,486 A | 8/1963 | Nehring | |
| 3,103,335 A | 9/1963 | Martinez | |
| 3,252,124 A * | 5/1966 | Hansen | 439/291 |
| 3,709,365 A * | 1/1973 | Czaplinski et al. | 210/233 |
| 4,059,512 A | 11/1977 | Harris | |
| 4,144,884 A | 3/1979 | Tersteegen et al. | |
| 4,202,332 A | 5/1980 | Tersteegen et al. | |
| 4,246,101 A | 1/1981 | Selby, III | |
| 4,370,983 A | 2/1983 | Lichtenstein | |
| 4,432,765 A * | 2/1984 | Oscarsson | 604/411 |
| 4,495,067 A * | 1/1985 | Klein et al. | 210/87 |
| 4,564,132 A * | 1/1986 | Lloyd-Davies | 222/522 |
| 4,596,550 A | 6/1986 | Troutner | |
| 4,626,240 A | 12/1986 | Edelman et al. | |

(Continued)

FOREIGN PATENT DOCUMENTS

DE    8305713    12/1985

(Continued)

OTHER PUBLICATIONS

Online encyclopedia article "Depyrogenation." Accessed Apr. 12, 2010. http://en.wikipedia.org/wiki/Depyrogenation.*

(Continued)

*Primary Examiner* — Tatyana Zalukaeva
*Assistant Examiner* — Philip R Wiest
(74) *Attorney, Agent, or Firm* — Miles & Stockbridge, P.C.; Mark A. Catan

(57) ABSTRACT

Blood treatment system and method for high rate hemofiltration ensures against pyrogenic patient reaction by providing various mechanisms for filtering replacement fluid to remove endotoxins and other safety features including detecting incorrect fluid administration.

16 Claims, 10 Drawing Sheets

U.S. PATENT DOCUMENTS

| | | | |
|---|---|---|---|
| 4,661,246 A | 4/1987 | Ash | |
| 4,711,715 A * | 12/1987 | Polaschegg | 210/103 |
| 4,784,495 A | 11/1988 | Jonsson et al. | |
| 5,139,483 A * | 8/1992 | Ryan | 604/86 |
| 5,221,483 A * | 6/1993 | Glenn et al. | 210/641 |
| 5,259,954 A | 11/1993 | Taylor | |
| 5,308,333 A | 5/1994 | Skakoon | |
| 5,368,555 A | 11/1994 | Sussman et al. | |
| 5,536,412 A | 7/1996 | Ash | |
| 5,591,344 A | 1/1997 | Kenley et al. | |
| 5,622,626 A * | 4/1997 | Matkovich et al. | 210/649 |
| 5,645,734 A | 7/1997 | Kenley et al. | |
| 5,662,642 A * | 9/1997 | Isono et al. | 604/403 |
| 5,690,831 A | 11/1997 | Kenley et al. | |
| 5,702,597 A | 12/1997 | Chevallet et al. | |
| 5,779,905 A | 7/1998 | Morandi et al. | |
| 5,782,762 A | 7/1998 | Vining | |
| 5,919,357 A | 7/1999 | Wilkins et al. | |
| 5,972,225 A | 10/1999 | Karras et al. | |
| 6,039,877 A | 3/2000 | Chevallet et al. | |
| 6,106,723 A * | 8/2000 | Grandics et al. | 210/651 |
| 6,132,616 A | 10/2000 | Twardowski et al. | |
| 6,136,201 A | 10/2000 | Shah et al. | |
| 6,146,536 A | 11/2000 | Twardowski | |
| 6,187,207 B1 | 2/2001 | Brauer | |
| 6,253,567 B1 | 7/2001 | Imanari et al. | |
| 6,254,567 B1 | 7/2001 | Treu et al. | |
| 6,284,142 B1 | 9/2001 | Muller | |
| 6,287,516 B1 | 9/2001 | Matson et al. | |
| 6,331,252 B1 | 12/2001 | El Sayyid et al. | |
| 6,428,518 B1 | 8/2002 | Brengle et al. | |
| 6,475,385 B1 | 11/2002 | Boyce et al. | |
| 6,561,997 B1 | 5/2003 | Weitzel et al. | |
| 6,572,576 B2 | 6/2003 | Brugger et al. | |
| 6,579,253 B1 | 6/2003 | Burbank et al. | |
| 6,582,385 B2 * | 6/2003 | Burbank et al. | 604/5.04 |
| 6,589,482 B1 | 7/2003 | Burbank et al. | |
| 6,595,943 B1 | 7/2003 | Burbank | |
| 6,626,857 B1 | 9/2003 | Ohta et al. | |
| 6,638,477 B1 | 10/2003 | Treu et al. | |
| 6,638,478 B1 | 10/2003 | Treu et al. | |
| 6,649,063 B2 | 11/2003 | Brugger et al. | |
| 6,743,193 B2 | 6/2004 | Brugger et al. | |
| 6,745,903 B2 * | 6/2004 | Grandics | 210/501 |
| 6,830,553 B1 | 12/2004 | Burbank et al. | |
| 6,852,090 B2 | 2/2005 | Burbank et al. | |
| 6,855,122 B1 | 2/2005 | Ohta et al. | |
| 6,955,655 B2 | 10/2005 | Burbank et al. | |
| 6,962,575 B2 | 11/2005 | Tal | |
| 7,214,312 B2 | 5/2007 | Brugger et al. | |
| 7,226,538 B2 | 6/2007 | Brugger et al. | |
| 7,322,969 B2 * | 1/2008 | Hattori et al. | 604/406 |
| 7,419,597 B2 * | 9/2008 | Brugger et al. | 210/646 |
| 7,473,238 B2 | 1/2009 | Brugger et al. | |
| 7,544,300 B2 | 6/2009 | Brugger et al. | |
| 2001/0016699 A1 | 8/2001 | Burbank et al. | |
| 2001/0021817 A1 | 9/2001 | Brugger et al. | |
| 2001/0037079 A1 * | 11/2001 | Burbank et al. | 604/6.09 |
| 2001/0039441 A1 | 11/2001 | Ash | |
| 2001/0048909 A1 | 12/2001 | Taylor | |
| 2002/0085952 A1 | 7/2002 | Ellingboe et al. | |
| 2002/0104800 A1 * | 8/2002 | Collins et al. | 210/646 |
| 2002/0167322 A1 | 11/2002 | He et al. | |
| 2002/0190000 A1 * | 12/2002 | Baurmeister | 210/650 |
| 2003/0010701 A1 * | 1/2003 | Collins et al. | 210/321.6 |
| 2003/0042201 A1 | 3/2003 | Sizelove et al. | |
| 2003/0051767 A1 | 3/2003 | Coccaro et al. | |
| 2003/0080140 A1 | 5/2003 | Neas et al. | |
| 2003/0105435 A1 | 6/2003 | Taylor | |
| 2003/0130606 A1 | 7/2003 | Tuck | |
| 2003/0168389 A1 | 9/2003 | Astle et al. | |
| 2003/0173297 A1 * | 9/2003 | Grandics | 210/650 |
| 2003/0236481 A1 | 12/2003 | Burbank | |
| 2004/0045881 A1 | 3/2004 | Collins et al. | |
| 2004/0060866 A1 * | 4/2004 | Radunsky et al. | 210/647 |
| 2004/0069709 A1 | 4/2004 | Brugger et al. | |
| 2004/0089594 A1 | 5/2004 | Collins et al. | |
| 2004/0186415 A1 | 9/2004 | Burbank et al. | |
| 2004/0222139 A1 | 11/2004 | Brugger et al. | |
| 2004/0232079 A1 | 11/2004 | Taylor et al. | |
| 2005/0045548 A1 | 3/2005 | Brugger et al. | |
| 2005/0103717 A1 | 5/2005 | Jha et al. | |
| 2005/0171501 A1 | 8/2005 | Kelly | |
| 2005/0209547 A1 | 9/2005 | Burbank et al. | |
| 2007/0007208 A1 | 1/2007 | Brugger et al. | |
| 2007/0038191 A1 | 2/2007 | Burbank et al. | |
| 2007/0260168 A1 | 11/2007 | Brugger et al. | |
| 2008/0053905 A9 | 3/2008 | Brugger et al. | |
| 2008/0210606 A1 | 9/2008 | Burbank | |
| 2008/0230450 A1 | 9/2008 | Burbank et al. | |

FOREIGN PATENT DOCUMENTS

| | | |
|---|---|---|
| DE | 19704564 | 8/1998 |
| GB | 2135598 | 9/1984 |
| WO | WO 96/36370 | 11/1996 |
| WO | WO 99/56696 | 11/1999 |
| WO | WO 02/32476 | 4/2002 |
| WO | WO 02/095675 | 11/2002 |
| WO | WO 03/006100 | 1/2003 |
| WO | WO 03/006139 | 1/2003 |
| WO | WO 03/103533 | 12/2003 |
| WO | WO 2004/062710 | 7/2004 |
| WO | WO 2004/066121 | 8/2004 |
| WO | WO 2004/080282 | 9/2004 |
| WO | WO 2004/084972 | 10/2004 |
| WO | WO 2005/068043 | 7/2005 |
| WO | WO 2006/074429 | 7/2006 |
| WO | WO 2007/118235 | 10/2007 |

OTHER PUBLICATIONS

FDA guidelines for Bacterial Endotoxins/Pyrogens. Accessed Apr. 12, 2010. http://www.fda.gov/ICECI/Inspections/InspectionGuides/InspectionTechnicalGuides/ucm072918.htm.*

Examination Report for European Patent Application No. 03 736 859, dated Nov. 11, 2008.

"Risk Free Connection of Pre-Sterilized Single Use Fluid Path Assemblies to Stainless Steel SIP Systems with Lynx ST (Steam-to) Connectors." Millipore Corporation Catalogue, May 2003.

Shipe, B. "The Case for UV in Dechlorination Applications." Water Conditioning and Purification Magazine, Jan. 2003, 45(1):pp. 34-36.

* cited by examiner

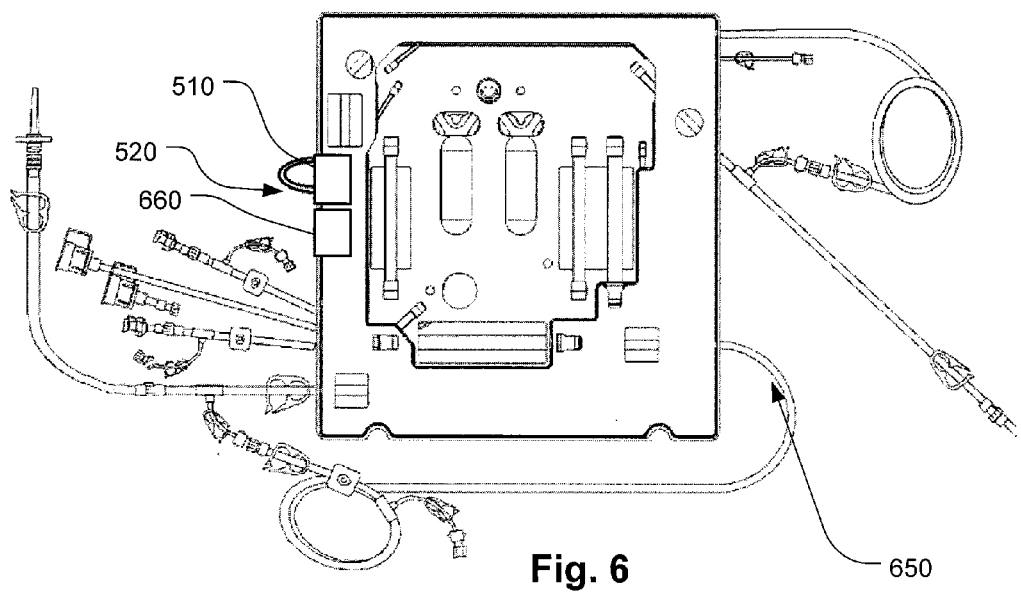
Fig. 6
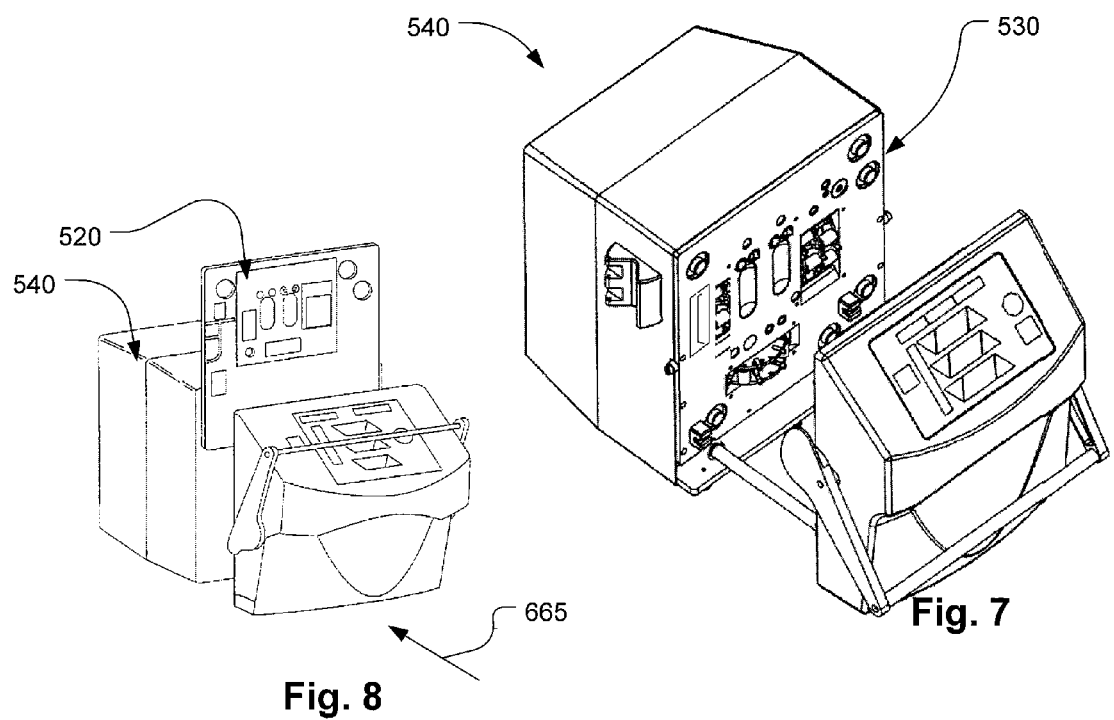
Fig. 8
Fig. 7

LAST-CHANCE QUALITY CHECK AND/OR AIR/PATHOGEN FILTER FOR INFUSION SYSTEMS

CROSS-REFERENCE TO RELATED APPLICATIONS

This application is a divisional of U.S. patent application Ser. No. 10/513,693, filed on Nov. 8, 2004, which claims the benefit of U.S. Provisional Patent Application No. 60/386,483, filed on Jun. 6, 2002, now expired, and U.S. Provisional Patent Application No. 60/438,567, filed on Jan. 7, 2003, now expired, and International Application No. PCT/US03/17743, filed on Jun. 5, 2003, all of which are incorporated herein by reference in their entireties.

BACKGROUND OF THE INVENTION

During hemofiltration, hemodialysis, hemodiafiltration, ultrafiltration, and other forms of renal replacement therapy, blood is drawn from a patient, passed through a filter, and returned to the patient. Depending on the type of treatment, fluids and electrolytes are exchanged in the filter between a dialysate and/or extracted from the blood by filtration. One effect may be a net loss of fluid and electrolytes from the patient and/or exhaustion of dialysate, with a concomitant need for its replenishment, again depending on the type of treatment. To replace fluid lost from the patient and keep the patient from dehydrating, replacement fluid may be injected into the patient at a rate that matches a rate of loss, with an adjustment for a desired net change in the patient's fluid complement. To replace exhausted dialysate, fresh dialysate is continuously circulated through the filter.

Presently methods to produce large volumes of dialysate from tap water are known, but each requires complex water purification and standardization equipment, since impurities and cleaning additives such as chlorine vary greatly in tap water from municipality to municipality and within a municipality over time. (See Twardowski U.S. Pat. Nos. 6,146,536 and 6,132,616.) Moreover, dialysate solution, whether prepared online or prepackaged, while of the proper concentration for use as a replacement fluid, is not directly infused into the patient's body. Instead, dialysate flows past a semipermeable membrane that permits ions and water to be exchanged across the membrane until a balance between their concentrations in blood and their concentrations in the dialysis is achieved. This is effective to remove impurities from the blood and to add missing electrolytes to the blood, but the volume of fluid that is infused is not as great as with hemofiltration.

Conventionally, dialysate and/or replacement fluid is supplied from either of two sources: batches of fluid, typically in multiple bags, or a continuous sources of water that is sterile-filtered and added to concentrated electrolytes to achieve the required dilution level. Because replacement fluid is injected directly into the patient, replacement fluid is required to be sterile and is recommended to have limited levels of pyrogens, particularly endotoxins, which are quantified in endotoxin units (EU). The maximum amount of endotoxin allowed in a parenteral product or medical device set by the US Food and Drug Administration (FDA) and United States Pharmacopoeia (USP) for drugs is 5.0 EU/Kg/hr, a rate taking into account the weight of the patient (in Kg.) and the rate of infusion. Currently, however, replacement fluid packaged such that it is regulated as a drug may have an endotoxin load of up to 0.5 EU/ml. This would limit the replacement fluid exchange rate for a 72 Kg. patient to less than 12 ml./min. To be safely infused, per these specifications, at higher rates, the fluid must be further filtered of endotoxins. Filtering to 0.03 EU/ml., a level that may be identified as "ultrapure," allows an infusion rate of 200 ml./min., which may be sufficient for high rate continuous hemofiltration therapy of the type described in the following pending US patent applications each of which is hereby incorporated by reference as fully set forth in its entirety herein.

Ser. No. 08/800,881, filed Feb. 14, 1997 for Hemofiltration System;

Ser. No. 09/451,238 for Nov. 29, 1999 for Systems and Methods for Performing Frequent Hemofiltration;

Ser. No. 09/512,929, filed Feb. 25, 2000 for Fluid Replacement systems & Methods for Use in Hemofiltration;

Ser. No. 09/513,564, filed Feb. 25, 2000 for Systems and Methods for Detecting Air in an Arterial Blood Line of a Blood Processing Circuit;

No. 60/438,567, filed Jan. 30, 2003 for Preparing Replacement Fluid by Means of Batch Filtration Prior to Treatment;

Ser. No. 09/513,910, filed Feb. 25, 2000 for Systems and Methods that Maintain Sterile Extracorporeal Processing Conditions;

Ser. No. 09/513,911, filed Feb. 25, 2000 for Synchronized Volumetric Fluid Balancing Systems and Methods;

Ser. No. 09/513,915, filed Feb. 25, 2000 for Systems and Methods for Controlling Blood Flow & Waste Fluid Removal During Hemofiltration;

Ser. No. 09/862,207, filed May 21, 2001 for Methods, Systems and Kits for the Extracorporeal Processing of Blood;

Ser. No. 09/865,905, filed May 24, 2001 for Fluid Processing Systems and Methods Using Extracorporeal Fluid Flow Panels Oriented Within a Cartridge;

Ser. No. 09/894,236, filed Jun. 27, 2001 for Hemofiltration System;

Ser. No. 09/900,362, filed Jul. 7, 2001 for Method and Apparatus for Leak Detection in a Fluid Line (Disconnect Sensor—Reverse Lines to Use Air Sensor on Arterial Line (Leak));

Ser. No. 09/905,246, filed Jul. 12, 2001 for Devices and Methods for Sterile Filtering;

Ser. No. 09/907,872, filed Jul. 17, 2001 for Hermetic Flow Selector Valve;

Ser. No. 60/324,437 filed Sep. 24, 2001 for Device and Method for Enhancing Performance of Membranes.

Ser. No. 10/040,659, filed Jan. 7, 2002 for Blood Treatment Replacement Fluid Using Infusible Fluids in Combination;

No. 60/346,458 filed Jan. 7, 2002 for Hemofiltration Filter with High Membrane Utilization Effectiveness; and No. 60/346,403 filed Jan. 7, 2002 for Hemofiltration System Method of Use and Associated Control System.

In many instances, blood treatment therapies may require a large quantity of sterile fluid. A typical way to provide the large quantity of replacement fluid is to provide multiple bags of replacement fluid, dialysate, or infusate. The connection of these bags of fluid to an extracorporeal blood circuit creates a risk of touch contamination resulting in the introduction of contaminants into the fluids. Contamination may occur, for example, at the point where bags of fluid are accessed ("spiked") or at other times during preparation for infusion such as when the patient is accessed.

Attempts to render dialysate suitable for use as a replacement fluid in hemofiltration and hemodiafiltration have focused on continuous sterilization processes that require a separate dialysate filtration/purification apparatus that must be periodically purged and verified to provide sufficient constant flow of sterile replacement fluid required for hemofiltration. (See Chavallet U.S. Pat. Nos. 6,039,877 and 5,702, 597.) Such devices are necessarily complicated and require separate pumping systems for the sterilization process. In addition, the rate of supply of dialysate for such systems is very high, requiring an expensive filter to be used. The same high-rate problem exists for the generation of replacement fluid for hemofiltration, and therefore also requires an expensive filter.

There is a need for improved mechanisms for providing safe economic replacement fluid for use in various blood therapies.

SUMMARY OF THE INVENTION

In the present invention, sterile, and preferably substantially non-pyrogenic (e.g., including endotoxin-free) replacement fluid or dialysate may be generated in batch form by filtering. According to various embodiments of inventions disclosed, 1. raw fluid is passed through a filter prior to treatment to prepare a batch of infusible replacement fluid;
2. raw fluid is passed by gravity feed during treatment through filters attached to infusion lines from each of one or more batch containers;
3. raw or prefiltered fluid according to either or both of the previous methods is passed through a last-chance filter immediately prior to injection into the patient.

Preferably, the filter has a pore size and quality effective to block endotoxins such that the replacement ultimately infused that is substantially less than 5 EU/Kg./hr (based on the rate of treatment), the limit set by the USP for parenteral drugs and no more than 0.5 EU/ml. Preferably the filter provides this degree of filtration with minimal pressure drop, for example by means of a relatively large pore size (e.g., 0.2 Micron) in combination with a charged nylon membrane which attracts endotoxins and helps to ensure against their passage. Filters are available with smaller pore sizes and may be used rather than relying on adsorption as with the nylon membrane example. For example pores sizes of 0.005 micron and somewhat larger will block most endotoxins. But small pore size implies high pressure drop and generates inefficiencies for production.

The raw (source) replacement fluid may be industry standard quantities of pyrogens and labeled as suitable for injection, the inventive method providing a higher degree of purity than is currently allowed for infusible fluids regulated either as medical devices or drugs.

The batch filtration process may be permitted to take any length of time because the rate of flow of raw replacement fluid (or components thereof) through the filter is completely independent of the rate of consumption by the renal therapy. Because the filters used for such filtering tend to be expensive, it may be desirable for such a batch process to employ a small pyrogen filter for such filtration. Such a filter can have a flow capacity that is much lower than that required for real-time filtering of the replacement fluid (or components). Alternatively, the fluid may be passed under pressure for a suitably supported membrane or strong membrane material adequate to permit real-time filtration as discussed elsewhere in the present specification. In addition to preparation of low pyrogen (preferably at least with low levels of endotoxins) fluid from sterile or non-sterile and/or pyrogen-purified fluid, embodiments of inventions disclosed may be used to ensure against touch contamination.

Treatment by hemofiltration requires the extraction from patients of a large volume of fluid compared to hemodialysis, although both perform similar functions. In hemodialysis, fluid and electrolytes cross a filter membrane into and out of the blood of the patient in response to a difference in concentration of electrolytes. Some net quantity of fluid may be taken from the patient if there is an excess in the patient's blood and some net quantity of replacement fluid may be infused directly if there is a paucity in the patient's blood. In hemofiltration, fluid is drawn out of the patient continuously and replaced with electrolytically-proper fluid. As a result, the quantity of fluid infused in the patient tends to be much greater than with hemodialysis and, coincidentally, most other types of infusion therapies including parental infusion therapies. In addition, new hemofiltration therapies have been developed which permit very fast continuous treatment, which may involve the infusion of replacement fluid at a very high rate. The risk of adverse reactions due to the infusion of pyrogens into patients increases with the dose and the period of time over which the infusion takes place. As a consequence, the allowed concentration of pyrogens in replacement fluid for hemofiltration should be substantially lower than for other treatments, for example for hemodialysis or other infusion therapies.

While low pyrogen levels may be achieved using sterilization and filtration techniques that are known, there are also a number of practical matters that are well to combine in addressing the problem of pyrogen infusion in hemofiltration. For example, even when highly purified replacement fluid is used for replacement fluid, touch-contamination can cancel any benefit of starting with a highly purified fluid.

In disclosed embodiments of blood treatments systems, including hemofiltration systems generally as well as high flow-rate hemofiltration systems particularly, the low pyrogen concentrations may be achieved by one or more features, including:

1. batch filtration of raw replacement fluid at the site of use and in a manner that minimizes risk of touch-contamination or other sources of recontamination;
2. filtration of raw replacement fluid at the site of use at the rate of consumption in real time during treatment, preferably with a filter located close to the point of injection so as to minimize the risk of downstream contamination;
3. filtration using filters that permit the passage of no more than 0.03 endotoxin units per ml.; and
4. filtration using filters using a combination of adsorption and blocking mechanisms to provide an optimal balance between pressure drop across the filter media and the need to block pyrogen particles, preferably with a charged nylon membrane, which attracts endotoxins thereby helping to block them and having an approximately 0.2 micron pore size.

Generally replacement fluid is heated before being infused into a patient. This is often accomplished by passing the fluid through a heater with enough heating capacity to heat the fluid as it is being infused. The capacity of the heater must be matched to the mass flow of the fluid and the temperature rise required. In a batch preparation process, where a batch of fluid is prepared over a substantial period before use, a small heater may heat the replacement fluid over a long period of time. Insulation may be provided to prevent heat loss. An insulating outer container for the source replacement fluid may be provided. For example, the container may be an insulated box with room for one or more large disposable sterile bags of the type normally used for infusible fluids.

The preparation of warm replacement fluid may be automated by a control process that permits a user to set up the fluids and other materials well in advance of a scheduled treatment. The process would ensure that the replacement fluid is treated to remove pyrogens and heated to the proper temperature when the treatment is to begin. The automation process may be permit the user to select how far in advance of the treatment the preparation should be performed. This may be useful, for example, where a particular source of replacement fluid has proved to release more than a usual quantity of dissolved gases upon heating. Heating the replacement fluid and permitting it to settle for a time before it is used may allow gases to come out of solution and settle at the top of the batch vessel or vessels. The automation process may be incorporated in the control functions of renal therapy machine.

The invention or inventions will be described in connection with certain preferred embodiments, with reference to the following illustrative figures so that it may be more fully understood. With reference to the figures, it is stressed that the particulars shown are by way of example and for purposes of illustrative discussion of the preferred embodiments of the present invention or inventions only, and are presented in the cause of providing what is believed to be the most useful and readily understood description of the principles and conceptual aspects of the invention or inventions. In this regard, no attempt is made to show structural details of the invention in more detail than is necessary for a fundamental understanding of the invention or inventions, the description taken with the drawings making apparent to those skilled in the art how the several forms of the invention or inventions may be embodied in practice.

BRIEF DESCRIPTION OF THE DRAWINGS

FIGS. 6-8 illustrate a blood treatment machine and cartridge providing various supporting mechanical features for the embodiment of FIG. 5 and further embodiments, including one in which a quality of replacement fluid is sensed before infusion.

DETAILED DESCRIPTION

Figure 1:
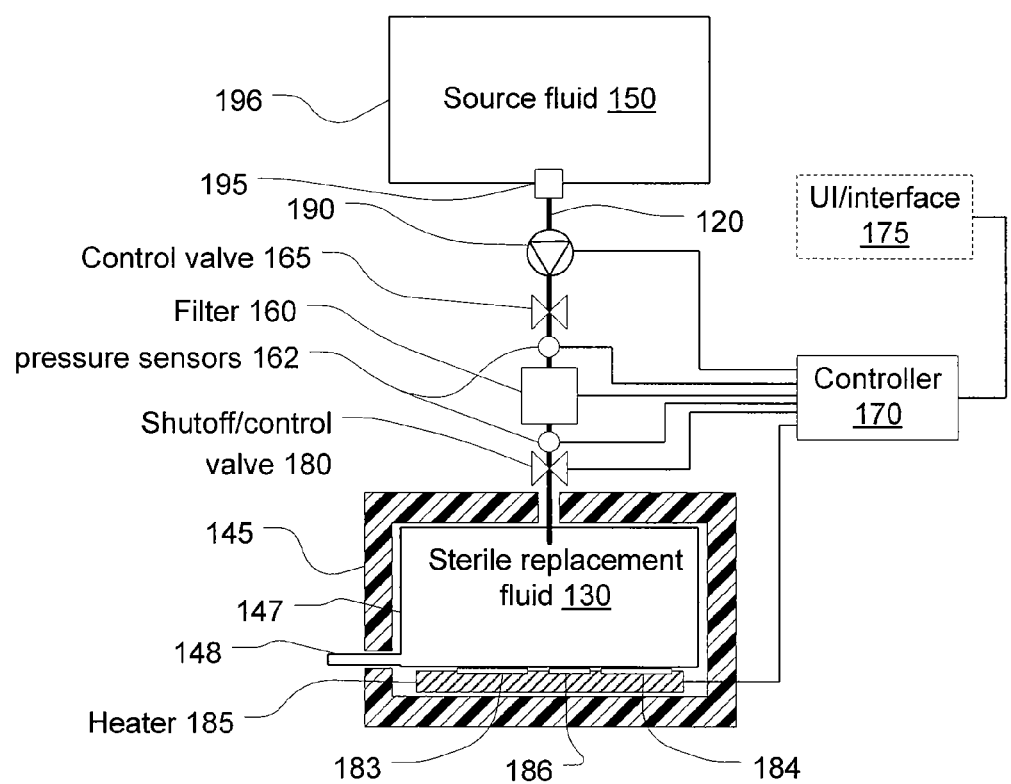
FIG. 1 is a schematic illustration of a standalone/retrofit apparatus system for batch filtration of a sterile, endotoxin-purified, or pyrogen-purified replacement fluid.

Referring to FIG. 1, a filter 160 filters fluid from a source of fluid 150 to generate a batch of infusible replacement fluid 130. The filter 160 may be, and preferably is, a microporous filter that blocks pyrogens and allows the passage of dissolved electrolytes and water. The latter may provide an infusible fluid free of all pyrogens, however, in practice, the pyrogen concentration must be reduced, but not necessarily eliminated since total elimination is not practical. The most common type of pyrogen is endotoxins, which may be present even in sterilized fluids.

In hemofiltration, a large quantity of fluid is drawn from the patient and replaced with replacement fluid. Compared to dialysis, the quantity actually removed and replaced with replacement fluid tends to be high. As a consequence, it is desirable to provide replacement fluid that has a lower concentration of pyrogens than may be allowed in other infusible fluids and what may cross the membrane of a dialysis system. Thus, a filter effective to reduce endotoxins to levels at least as low as 0.03 endotoxin units per 25 ml. should be provided for the filter 160.

The result of the filtration process is the sterilization and cleansing of endotoxins and particulate pyrogens in the raw fluid from the source of fluid 150. The source of fluid 150 may be a container 196 of fluid approved for injection or non-sterile replacement fluid. It may also be one or more containers of constituents which, when combined, form a proper replacement fluid (not shown) or a continuous source such as a tap water that is combined or has been combined with electrolyte concentrate (not shown). The starting fluid may be a function of the type of filter 160 used. For example, when processing fluid with a relatively large concentration of particulate pyrogens, for example bacteria, it is desirable to use a very large filter to ensure that its filtering performance is not compromised. In a preferred embodiment, a small replacement filter is used (since they tend to be costly) and the source fluid is fluid that has already been filtered to achieve low levels of pyrogens.

One or more conduit elements form a line 120 to convey the source fluid 150 through the filter 160 and into a batch container 147. The latter may be any type of sterile, preferably disposable container, for example, a large IV bag. It may also include a number of such containers appropriately interconnected to permit flow into and out of them in the fashion of container 147.

Included in the conveyance from source fluid 150 to infusible replacement fluid 130 may be a pump 190, such as a peristaltic pump. The pressure at an outlet of the filter 160 may be sensed by a pressure sensor 162 and the pump 190 controlled by a controller 170 to insure a predefined transmembrane pressure (TMP) threshold of the filter 160 is not breached. The TMP may be maintained at a maximum safe level to maximize throughput. Note that complexity may be avoided if the source fluid 150 is arranged such as to maintain a desired TMP at the filter 160 without the need of a pump 190 or pressure sensor 162. For example, the source fluid 150 may be provided by a batch container elevated at a certain height to provide a desired head. Note that a control valve 165 or a speed of the pump 190 may be used to regulate the flow rate to maintain desired TMP limits.

A control/shutoff valve 180 may provide the controller 170 the ability to stop the flow of fluid through the filter 160 once a desired volume is reached. A heater 185 may be provided to warm the filtered replacement fluid 130 to prepare it for use. An insulated container 145 may be used to reduce heat loss so that heater 185 can be a relatively low power type. The heater 185 may be controlled by the controller 170 to ensure the replacement fluid 130 is at a desired temperature when required to be used. Alternatively the heater 185 can be controlled by an independent device actuated by, for example, a pressure sensor (for example as shown at 186 in FIG. 1) triggered by the flow of fluid into the batch container 147, a timer (not shown) settable to trigger based on a predefined treatment time, or some other means. Preferably, in either case, a temperature regulator (e.g., a temperature sensor 183 combined with logic in controller 170) regulates power to the heater to ensure a required temperature is maintained and not exceeded. The temperature sensor 183 may be used to sense the quantity of filtered replacement fluid by the rate of detected temperature increase versus heater output. The temperature sensor 183, heater 185, and filtered replacement fluid 130 can be modeled in any desired fashion. For example one may neglect all but the thermal mass of the RF, assume perfect heat transfer (including assuming the RF fluid to be isothermal). Then, the mass is given by the product of the temperature change, the thermal capacitance of the fluid, and the heat output rate of the heater. More complex theoretical or empirical algorithms would be a simple matter to derive and implement, for example the temperature variation can be fitted to the transient exponential that governs for instantaneous uniform heating from a plane source as the heater is started, taking temperature data points before substantial convection starts. The mass may also be determined by means of a contact-type pressure sensor 186 (e.g., strain gage attached to a bendable plate and calibrated against mass). Once the mass of fluid is calculated to be below a certain level, the controller 170 may be programmed to respond in accord with the assumption the filtered replacement fluid is exhausted. Equivalently, the controller 170 may simply respond to some predefined rate of temperature rise of the temperature sensor 183.

When the temperature of the filtered replacement fluid 130 is raised, dissolved gas may come out of solution. This may cause bubbles to accumulate inside the replacement fluid container 147, which is undesirable because of the risk of infusing bubbles into the patient's bloodstream. To help ameliorate that problem, a vibrator or ultrasonic transducer 184 may be provided to cause bubbles to coalesce and rise to a top of the container 147. As a result, bubble-free replacement fluid may be drawn through the outlet 148.

A connector 195 may be provided for connecting the source fluid to the line 120. The connector may be a luer, spike, threaded adapter, or any other suitable type. Although the various controls indicated above are shown to be controlled an automatic controller 170, each may be controlled also by manual mechanisms.

The FIG. 1 embodiment allows replacement fluid to be prepared in batch for later use. Thus, the rate of filtration of replacement fluid need not match the requirements of the treatment process or preparatory steps such as priming. As a result, a low capacity filter may be used for the filter 160. For example, typically only a small quantity of expensive media is required to make a small-capacity filter and as such, the cost of a low capacity filter can be much smaller than a high capacity filter. Also, other features found in high capacity filters, such as a large ratio of media surface to volume of the filter module are achievable only by means of folding or forming media into shapes that can be difficult to manufacture, such as tubes. Thus, savings can be achieved in simplification of the configuration of the filter as well. Relatively small filters with simple planar media held in plastic casings are available and suitable for this purpose.

The configuration of FIG. 1 may be retrofitted for use with an existing treatment system. For this purpose, the outlet 148 may be provided with any required connection adapter. A user interface 175 for entering data into the controller 170 may be provided as well.

Figure 2:
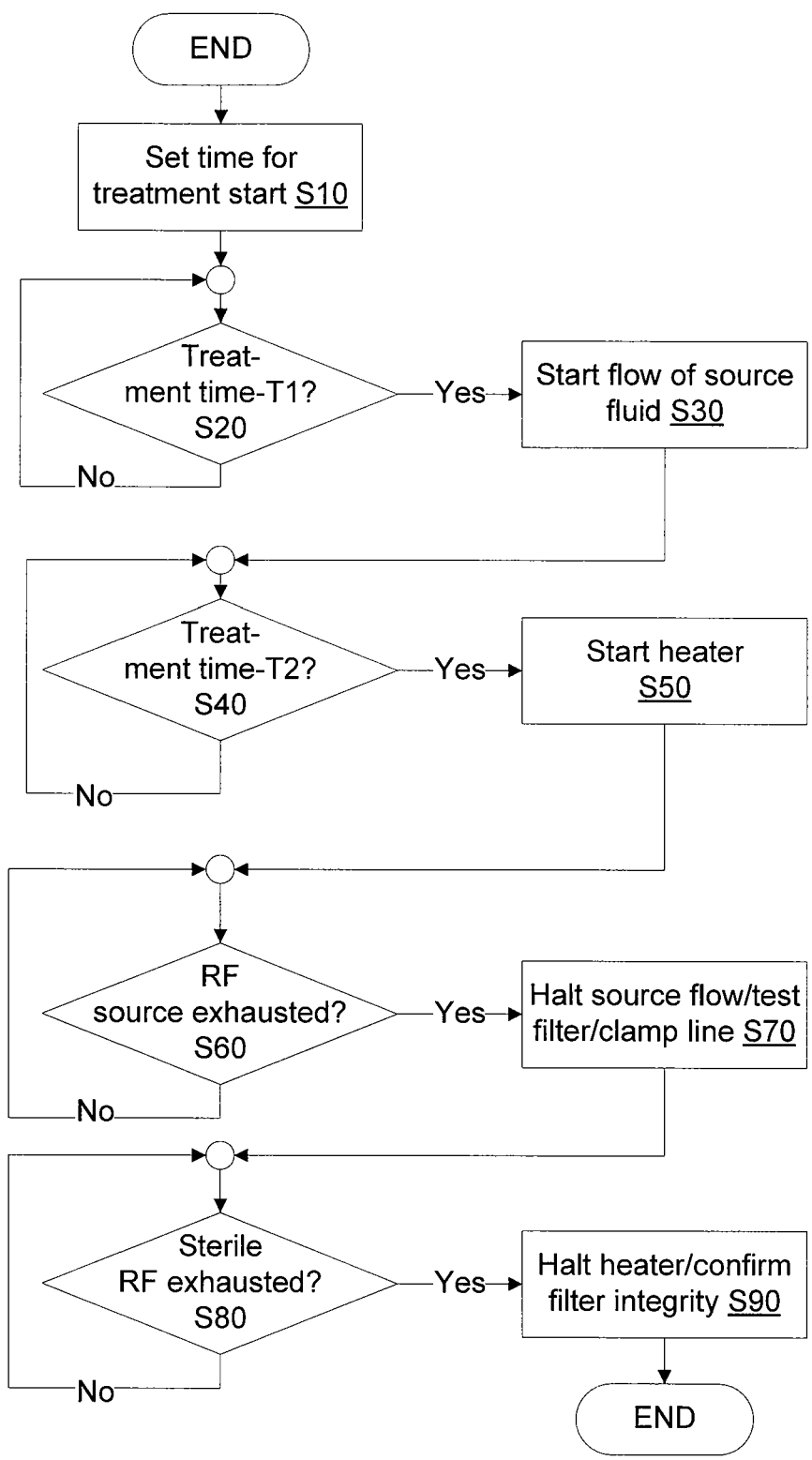
FIG. 2 is a flow chart illustrating an exemplary control procedure applicable to various embodiments of the invention including those of FIGS. 1 and 3.

Referring now also to FIG. 2, a control algorithm for controlling the heater 185, pump 190, valves 165/180, etc. begins with the a setting of a time for treatment S10, for example by entering a time into the controller 170 via a user interface (UI) 175. The time can be entered manually or automatically by means of, for example, a data signal from a remote source via a switched or network circuit. The time for treatment may be obtained from a treatment calendar entered into the controller 170, which also may be obtained from a remote source. In the present simple algorithm, first and second time intervals T1 and T2 are defined representing the interval required for filtration of RF and the interval required for heating of RF, respectively. These values may be obtained from any of the above means (e.g., local manual or remote entry via UI/interface 175) or from data encoded on one of the consumables involved in the process. For example, the filter 160, the RF fluid container 147, the source fluid 150 container(s), or any other consumable may be provided with one or more barcodes, RFID tags, or other suitable encoding device. Such devices may provide values for T1 and T2, tables of values that depend upon other factors, or other data from which T1 and T2 may be derived.

The controller 170 waits until it is time to start the flow of raw RF fluid from source fluid 150 toward container 147 by comparing a current time (indicated by a clock internal to the controller 170, which is not shown) to a difference between a scheduled treatment time and T1, which represents the lead time (ahead of the scheduled treatment) required for the filtering process. A loop through step S20 is exited to step S30 when the clock reaches the treatment time minus T1. At step S30, the flow of source fluid 150 through the filter 160 is initiated. If the pump 190 is present, it may be started and regulated according to a specified TMP. The latter may be provided to the controller 170 manually or automatically through UI/interface 175. Automatic entry may be by way of a data store such as bar-code or RFID attached to the filter, for example which may be read when the filter 160 is installed in a chassis with a corresponding reader device (not shown). Note, as mentioned above, the source fluid may be sterile and the filtration process provided as a guarantee against contamination, for example by accidental touching.

Once the flow of source fluid 150 is initiated, the controller waits for the required time for applying power to the heater 185. The delay and the initiation are controlled by step S40 which is exited to step S50 only when the treatment time minus the predefined interval T2 is reached. Note that the delay may also be zero. As mentioned above, alternatively, the heater may be triggered by detecting fluid such as by means of a sensor 186 of FIG. 1 (not shown) triggered by the presence of filtered replacement fluid 130 in the container 147. The sensor 186 may be any of a variety of types, such as an ultrasonic sensor, capacitance sensor, mass sensor, optical sensor, etc.

Once the heater is started, the controller 170 may wait for the source fluid to be exhausted at step S60. Step S60 exits to step S70 when the source fluid is determined to be exhausted. The latter may be detected by integrating the flow rate to measure the total volume (the rate may be determined by the pumping rate, for example, or by a flow meter (not shown)). The exhaustion of the source fluid 150 may also be indicated by a quantity indicator (e.g., a level indicator) in the filtered replacement fluid container 147 or an intermediate container supplied through a drip chamber, for example. Alternatively, the exhaustion of the source fluid 150, if supplied from a fixed-volume container, may be indicated by a sensor such as an ultrasonic sensor, capacitance sensor, mass sensor, optical sensor, a scale, etc. Yet another alternative is to sense gas or a precipitous rise in negative pressure (sensed by a pressure sensor which is not shown) at the pump 190 inlet. At step S70, the line 120 may be clamped by actuating shutoff/control valve 180. Additionally, if appropriate, the pump 190 may be deactivated at the point where the exhaustion of the source fluid 150 is detected at step S70.

According to an embodiment, as the fluid is pumped, the TMP of the filter, as indicated by pressure sensors 162, may be monitored. If the TMP is determined by the controller 170 to be, at any point, below a predetermined nominal value or to have changed precipitously during filtration, the controller 170 may trigger an alarm or take some other action to insure that the resulting replacement fluid is handled appropriately. For example, a back-up filter could be added during treatment as discussed with respect to FIG. 5. The TMP results could trigger an alarm at any point during filtration or could be assessed and reported at step S70, before treatment would begin.

The controller 170 pauses again at step S80 to wait for the sterile fluid to be exhausted. This may be indicated by a signal from the treatment machine (e.g., received via UI/interface 175) or by direct measurement by a sensor, such as an ultrasonic sensor, capacitance sensor, mass sensor, optical sensor, a scale, etc. As mentioned above, the controller 170, or the heater 185 itself, may be provided with a threshold temperature-rise rate that indicates the mass of fluid in the replacement fluid container 147 has fallen below a minimum level. The loop of step S80 is exited to step S90 where power to the heater 185 is terminated.

Note that all the functionality of the controller 170 may be provided, via a control interface, by a controller (not shown) internal to a treatment machine. For example, the apparatus of FIG. 1 could be provided as an optional module for such a treatment machine rather than a retrofit module.

Figure 3:
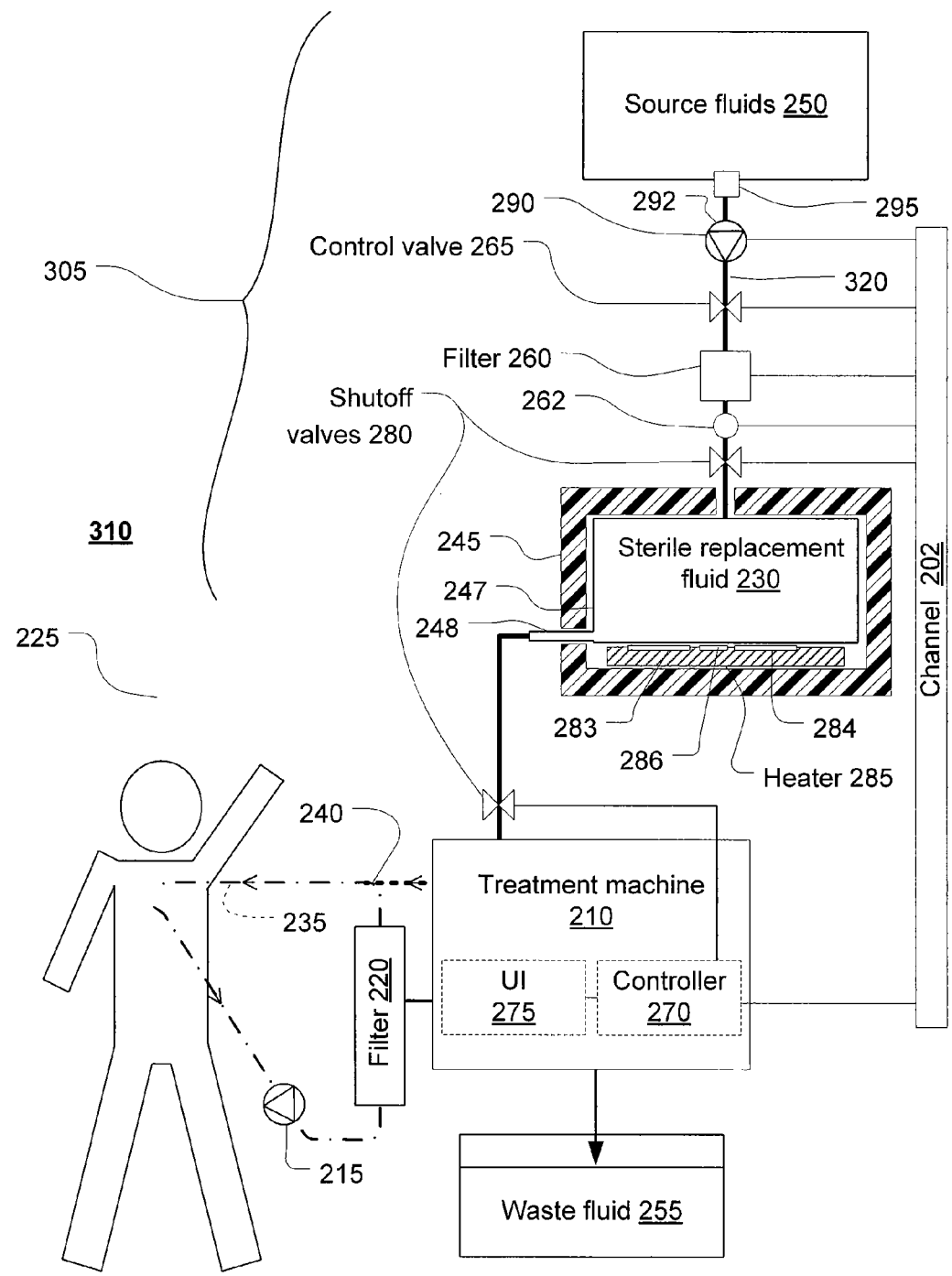
FIG. 3 is a schematic illustration of a blood treatment machine with an attached subsystem for batch preparation of infusible replacement fluid.

Referring now to FIG. 3, a combination blood treatment system and filtered replacement fluid device 310 has a replacement fluid preparation subsystem 305 configured substantially as the device of FIG. 1. A filter 260 filters fluid from a source of fluid 250 to generate a batch of filtered replacement fluid 230 as in the embodiment of FIG. 1. Again, the source of fluid 150 may be a container of purified or unpurified replacement fluid, one or more containers of constituents which, when combined, form a proper replacement fluid and any of the latter may include a continuous source such as a water tap. A line 320 conveys the source fluid 250 through the filter 260 and into a batch container 247, which may be any type of sterile, preferably disposable container, for example, a large IV bag. It may also include a number of such containers appropriately interconnected to permit flow into and out of them in the fashion of container 247.

Again, a pump 290 may be provided and pressure at an outlet of the filter 260 may be sensed by a pressure sensor 262. The pump 290 may be controlled by a controller 270 to insure a maximum safe TMP to maximize throughput. Again, the pump 290 is not required and the source fluid 250 may be arranged such as to maintain a desired TMP at the filter 260 without the need of the pump 290 or pressure sensor 262 by elevation. A control valve 265 or a speed of the pump 290 may be used to regulate the flow rate to maintain desired TMP limits.

A control/shutoff valve 280 may provide the controller 270 the ability to stop the flow of fluid through the filter 260 once a desired volume is reached. A heater 285 may be provided to warm the filtered replacement fluid 230 to prepare it for use. An insulated container 245 may be used and the heater controlled using a temperature sensor 283 as discussed with respect to the FIG. 1 embodiment. Bubbles may be controlled, as discussed above, by means of a vibration or ultrasonic transducer 284 and remaining fluid by means of pressure sensor 286.

A connector 295 may be provided for connecting the source fluid to the line 320. The connector may be a luer, spike, threaded adapter, or any other suitable type. Although the various controls indicated above are shown to be controlled an automatic controller 270, each may be controlled also by manual mechanisms. Other aspects of the control mechanisms for the embodiment of FIG. 3 may be provided as discussed with respect to FIGS. 1 and 2.

The benefits of the FIG. 3 embodiment are similar to those of the FIG. 1 embodiment in that it allows replacement fluid over a time period that is not driven by the speed of supply to the treatment process. As a result, a low capacity filter may be used for the filter 260 with the attendant benefits identified above. Note that the UI/interface 275 and controller 270 are shared in the present embodiment by the treatment machine. Thus, any information required for control of both the treatment and preparation of filtered replacement fluid 230 would not need to be communicated to a separate controller such as controller 270. Note also that the communications among the illustrated components is provided by a channel 202 which may be wire harness, separate wires, a bus, a wireless channel or any suitable communications/power transmission device.

In the embodiment of FIG. 3, a predicted quantity of replacement fluid may be filtered and stored for use during treatment. If, however, for some reason, more is required, the treatment machine controller 270 could be configured to identify that situation and control the subsystem 305 components to provide it. Many blood treatment process employ a filter 220 to filter blood and into which replacement fluid is supplied to a patient 225. More details on preferred embodiments of the treatment machine are discussed below.

In either of the above embodiments, the rate of flow of fluid during preparation of the batch of replacement fluid may be substantially less than the rate of consumption during treatment. In an exemplary embodiment of an application for hemofiltration, the amount of replacement fluid consumed is between 9 and 18 l. and the rate of consumption is approximately 200 ml./min. For daily treatment, a higher quantity of fluid is required. Also, the media used for sterile filtration may be any suitable media that insures the quality of the replacement fluid is as desired. In the embodiments discussed above, it was assumed that the end sought was preparation of filtered replacement fluid employed microfiltration to prevent the passage of pyrogens including endotoxins and any other pyrogens. However, the invention could be used with other types of filtration or treatment processes to produce a batch of fluid consumed by a medical treatment process, for example, dialysate for hemodialysis treatment. The benefits accrue in particular when the time scale of preparation may be longer than the time scale of consumption. Moreover, the benefits are more appreciable when some sort of energy-consuming process is required, such as heating, before consumption. Here, not only is the time scale of preparation compatible with a small inexpensive filter, but the long time scale permits heating of the replacement fluid over a long interval. To support this benefit, the batch container may be insulated to minimize heat loss so a small heater will be adequate. Also, the preferred application for the present invention is in the context of hemofiltration because the quantity of fluid required for such treatment is relatively small.

Note that other motivations for filtering the fluid, in addition to or as an alternative to sterilization of a non-sterile fluid, is (1) removal of air bubbles and/or (2) as a safety net for ensuring against accidental contamination. If bubble removal is the only concern, a drip chamber may be used instead of a filter. For removing bubbles, the filter preferably is of a type that permits the passage of fluid, but which blocks the passage of bubbles, for example due to its media pore size and the surface tension of the fluid.

Figure 4:
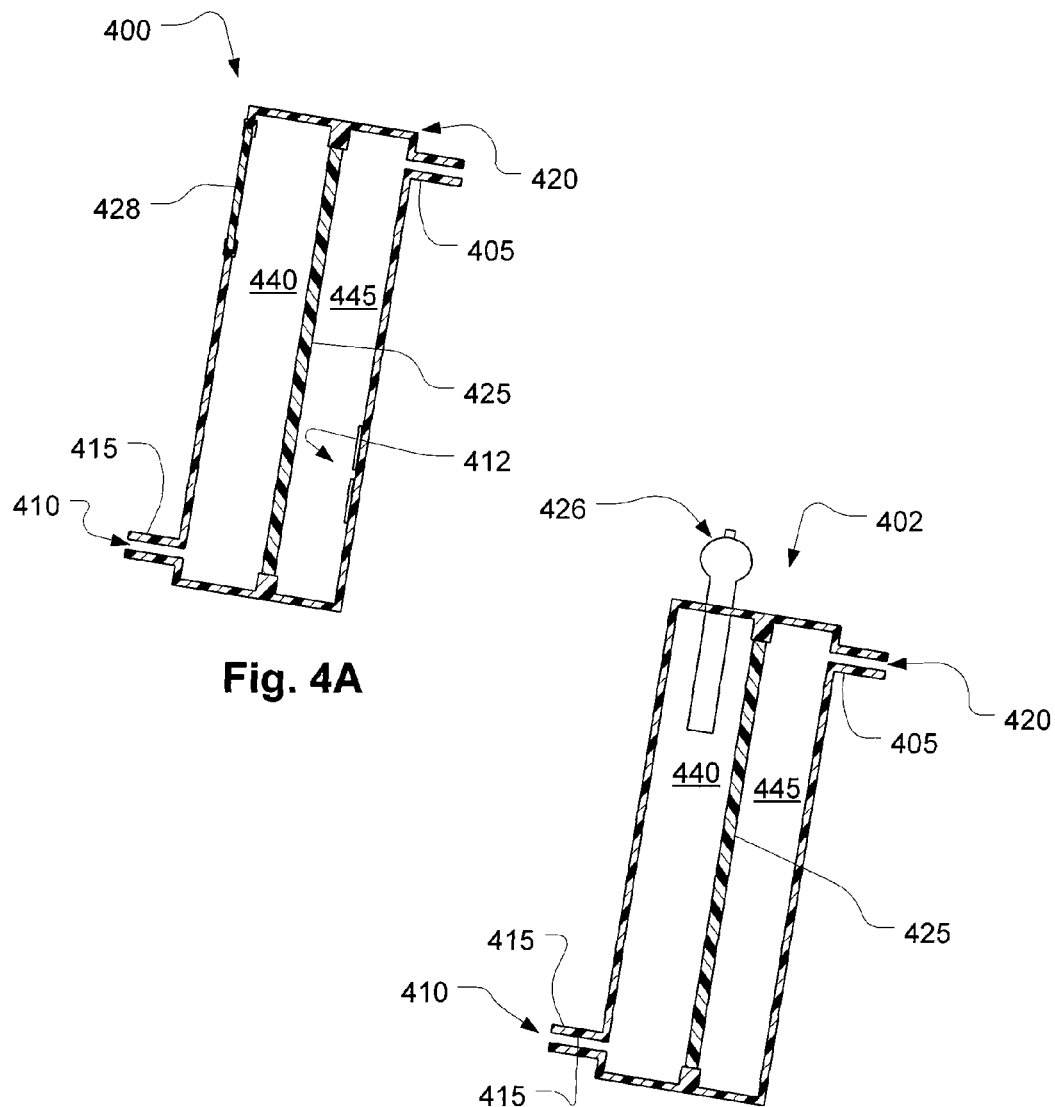
FIGS. 4A and 4B are illustrations of fluid filters that may be used in various embodiments of the invention.

Referring now to FIG. 4A, a preferred type of filter 400 for some of the present embodiments has an inlet port 415 providing an inlet channel 410 communicating with an inlet chamber 440. An outlet leading port 405 provides an outlet channel 420 communicating with an outlet chamber 445. A piece of filter media 425 separates the inlet and outlet chambers 440 and 445. The fluid to be sterilized enters the inlet chamber 440, is sterilized by passing through the filter media 425, and exits via the outlet chamber 445. A gas relief gasket 428 allows gas accumulating in the inlet chamber 440 to be released to the ambient atmosphere. Internal supports and structural details are not shown in the illustration for clarity, but a practical embodiment of the filter of FIG. 4 may have ribs for strength and internal supports for the media 425 and gasket 428 so that the filter 400 may be capable of tolerating a substantial TMP.

An integrated contact sensor 412 may be incorporated in the filter to sense the quality of the fluid such as its salinity. The illustration shows a pair of conductive contacts which, as will be understood by those of skill in the art, may be connected to a conductivity measuring device to generate a signal. Note that the sensor 412 could also include a non-contact type sensor such as an induction type device.

The gas relief gasket 428 may be of a porous hydrophobic material such as PTFE. Air bubbles trapped in the inlet chamber 440 can coalesce in the inlet chamber 440 and exit via the gas relief gasket 428. It may be, depending on the type of gas relief gasket 428 used, that a substantial TMP will be required to eliminate air.

An alternative to the gas relief gasket 428 is a gas relief valve 426 as shown in FIG. 4B. Since the inlet chamber 440 is connected to the non-sterile side of the filtration system, there is little risk of contamination if microbes were to enter through a mechanical device such as the gas relief valve 426. The latter is illustrated figuratively and allows only gas to escape. Other features of the embodiment of FIG. 4B are labeled with the same numerals as features of the embodiment of FIG. 4A where they serve substantially identical functions and, thus, their descriptions are not repeated here.

Figure 5:
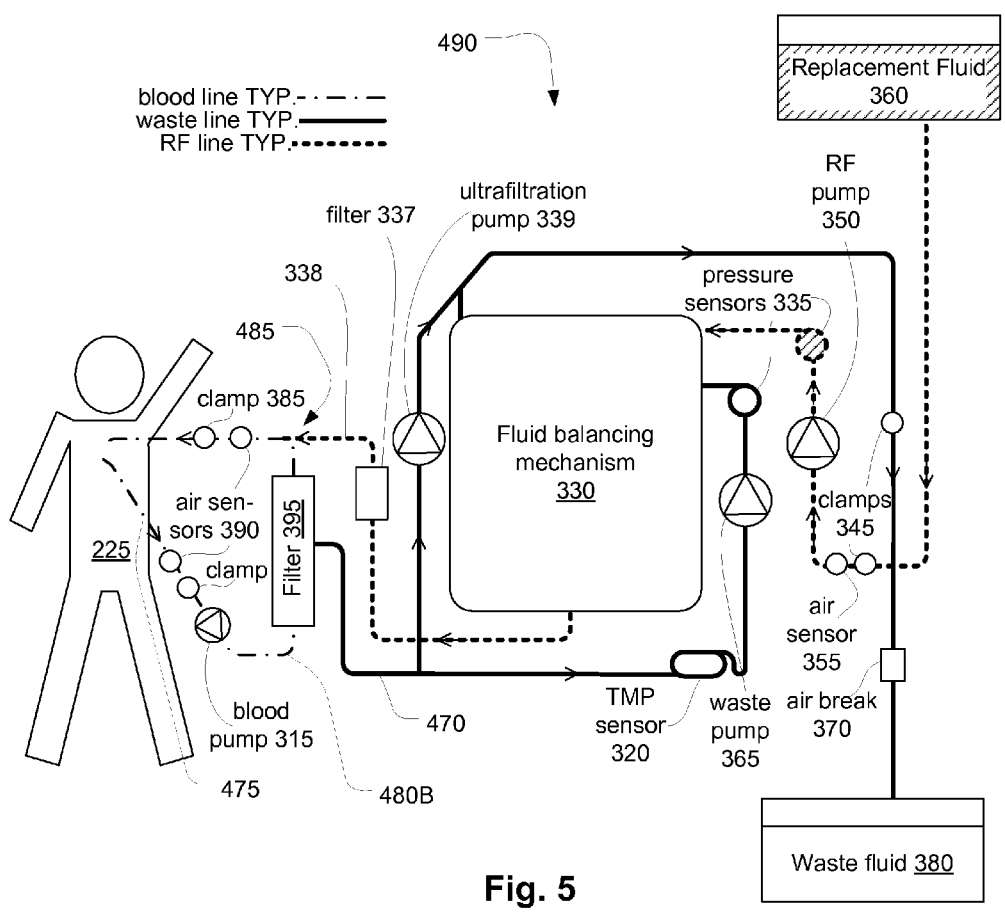
FIG. 5 illustrates an exemplary blood treatment system with a filter used to filter gas, pyrogens, endotoxins, or pyrogens from replacement fluid during treatment.

Referring now to FIG. 5, the filters of FIGS. 4A and 4B may be used for filtration of replacement fluid in the embodiment of FIG. 5 as discussed presently. Replacement fluid 360, which may or may not be sterile, is supplied to a hemofiltration machine 490. A replacement fluid pump 350 pumps the replacement fluid into a balancing mechanism 330 which meters the replacement fluid before it is introduced, via a junction 485, into the venous (return) line 480 and ultimately into the blood stream of a patient 225. Note that a common alternative configuration dilutes the arterial blood at 480B before it enters the filter 395. Waste fluid is drawn through a waste line 470 from a filter 395 and pumped via a waste pump 365 through the fluid balancing mechanism 330. The fluid balancing mechanism 330 meters the replacement fluid to match the rate of withdrawal of waste fluid so that the patient's fluid balance is maintained during treatment. Actually, the rate of withdrawal of waste fluid may be greater than the rate of metering of replacement fluid by pumping waste fluid through a bypass pump called an ultrafiltration pump 339. The latter sends some of the waste fluid directly to a waste fluid sump 380, thereby bypassing the fluid balancing mechanism 330. The fluid balancing mechanism is depicted figuratively and may operate in accord with any suitable control device. Preferably it meters replacement fluid on an equal-volume or equal-mass basis. A preferred mechanism is described in U.S. patent application Ser. No. 09/513,911, filed on Feb. 25, 2000, entitled: "Synchronized Volumetric Fluid Balancing Systems and Methods," which is hereby incorporated by reference as if fully set forth in its entirety herein. Various sensors and line clamps, indicated figuratively at 335, 355, 320, 385, and 390, may be provided to control flow and ensure safe operation.

A filter 337 is provided in the replacement fluid line 338 just upstream of the junction 485. The filter 337 may serve as a last chance safety net for ensuring that replacement fluid is sterile and/or that all bubbles are removed before flowing into the venous line 480. To ensure that air is not infused into the patient's body, an air sensor 390 is often provided in hemofiltration systems, but detection of air normally triggers an alarm, automatic shutdown, and skilled intervention to restart the hemofiltration treatment. Obviously, this is undesirable so the system should, as effectively as possible, insure that air or other gas is not injected into the venous line 480 without requiring interruption.

Although the embodiment of FIG. 5 includes a hemofiltration machine, other types of treatment processes may be provided a last-chance filter similar to filter 337 and air sensor 390. For example, hemodiafiltration, hemodialysis, or other treatments may require the infusion of replacement fluid and thereby benefit from a filter such as filter 337. Preferably, the filter 337 is substantially as in the embodiment of FIG. 4A. Thus, the filter 337 removes both air and pyrogens.

Instead of employing a filter at the location indicated at 337, a drip chamber may be used. Suitable drip chambers are currently available with air vents and microfilters effective to remove pyrogens, so they may be substituted for the filter 337. Also, in some cases, it may be that there is very little risk that the replacement fluid is contaminated with pyrogens, the filter 337 may serve as a mechanism for removing only air or other gases. In such cases, drip chambers which remove gas (either with or without a vent), could be employed at the above location in the fluid circuit.

Referring now to FIGS. 6, 7, and 8 the last chance filter or drip chamber (or combination device) 510 may be installed in a cartridge 520 that holds and orients blood and fluid circuits for a hemofiltration machine 540. In the embodiment shown, which is described substantially in U.S. patent application Ser. No. 09/513,773, filed Feb. 25, 2000 and entitled: "Fluid Processing Systems and Methods Using Extracorporeal Fluid Flow Panels Oriented Within A Cartridge," hereby incorporated by reference in its entirety as if fully set forth herein, fluid circuit components may be held in a cartridge 520 and clamped (as shown in FIG. 8 with the machine closing as illustrated by the arrow 665) within a receiving gap 530 in a blood treatment machine such as hemofiltration machine 540. The cartridge 520 may have a preferred orientation which may insure a correct orientation for the last chance filter or drip chamber (or combination device) 510 if required by the particular device chosen. To insure orientation of the last chance filter or drip chamber (or combination device) 510, the latter is preferably held by the cartridge 520 in a fixed orientation with respect to the cartridge 520.

In an alternative embodiment, the last chance filter or drip chamber (or combination device) 520 may be accompanied by a device 660 for measuring the quality of the replacement fluid, such as conductivity or density. This may provide a last-chance check that the replacement fluid is of the correct type. For example, where such fluids are derived from mixtures, if the proportion is not exactly what is required, infusion could be harmful to the patient 225. An example of a device 660 to test the fluid could be a wettable pair of contacts (not shown) formed in a tubing set 650 of the cartridge may be used in conjunction with a resistance measurement device to measure the ion concentration of the fluid. Alternatively, a non-wettable sensor, such as an inductive conductivity cell could be used. Other kinds of fluid quality sensors could be employed such as specific-molecule detectors built on silicon wafers and temperature sensors.

Preferably, the tubing set 650 and cartridge 620 of which it is a part form a disposable component that is used for one treatment and disposed of. Note that the fluid quality sensor 660 may used alone or together with the last chance filter or drip chamber (or combination device) 510. Note, although FIGS. 6 and 7 are detailed, they are intended to show various components figuratively and do not reveal the details of the routing necessary to achieve the flow paths discussed with respect to them or as illustrated elsewhere.

Figure 9:
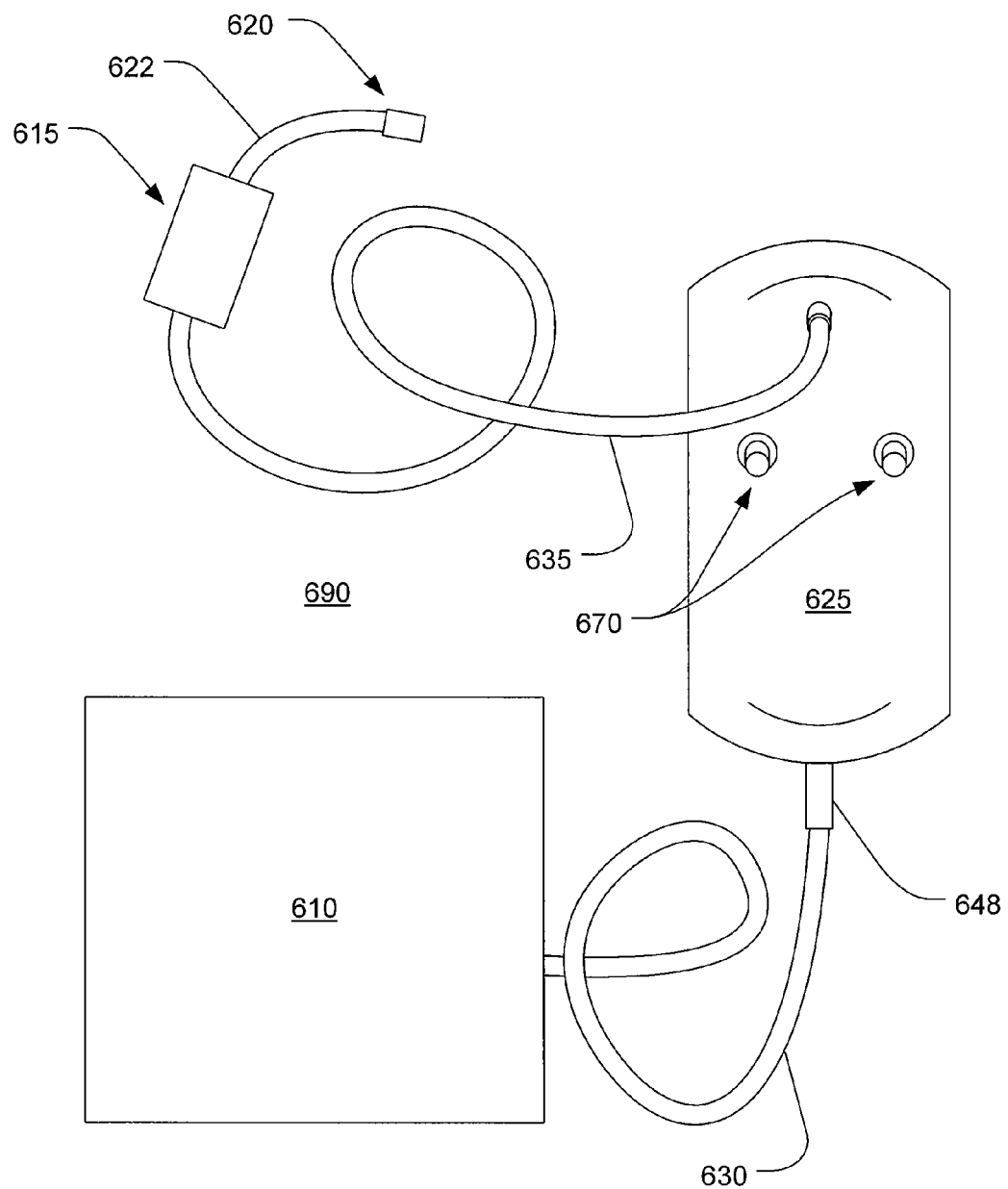
FIG. 9 illustrates a disposable fluid circuit kit which may support various embodiments of the invention.
Figure 10:
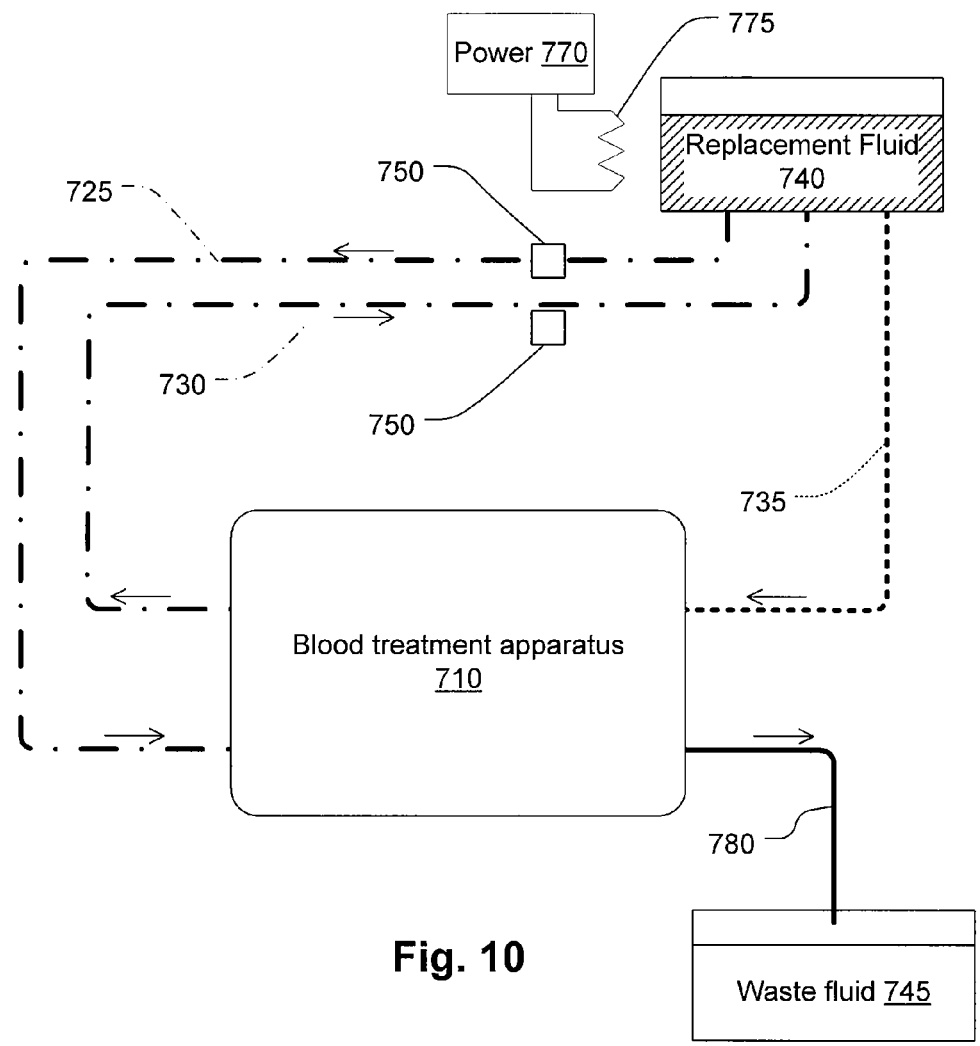
FIG. 10 illustrates a set up for priming a blood treatment process, which components of the invention may be used to support.

Referring now also to FIG. 9, the tubing set and cartridge assembly 610, discussed previously, may incorporate the batch replacement fluid container 625 as part of a sterile replaceable set 690. The filter 615 may have a tube 622 with a connector 620 for attachment to a source fluid 250. A tube 635 may connect the filter to the batch replacement fluid container 625, which may be fitted with another tube 630 connected by a connector 648, which may be permanent or removable, to convey fluid to the tubing set and cartridge assembly 610. Referring now also to FIG. 10, the batch replacement fluid container 625 may also be fitted with additional connectors 670 and/or extensions (not shown) to permit the batch replacement fluid container to be used for priming blood, replacement fluid, and/or waste lines. For example, as discussed in U.S. patent application Ser. No. 09/905,246, filed Jul. 12, 2001, entitled: "Devices and Methods For Sterile Filtering of Dialysate," which is hereby incorporated by reference as if fully set forth in its entirety herein, replacement fluid is circulated through a replacement fluid container 740 to flush air out of all the fluid circuiting (not all shown) of a blood treatment apparatus 710. As described in detail in the '246 application incorporated by reference above, the venous (return) and arterial (supply) blood lines 725 and 730 may be temporarily connected via connectors 750 to the replacement fluid container 740 and fluid circulated through the container 740 until gas bubbles are substantially purged from the corresponding circuits. Note, the replacement fluid container 740 corresponds to the containers 147 (FIG. 1), 247 (FIG. 3), and 625 (FIG. 9) in the foregoing figures and to respective containers in the application incorporated by reference immediately above. The air and other gases may settle in the replacement fluid container 740 as the fluid circulates. Liberation of the gases would ordinarily be promoted by the application of heat from a heater 775 (with power source 770), which may be employed as discussed with regard to the embodiments of FIGS. 1-3 or in any suitable way to bring the temperature of the replacement fluid to body temperature. Replacement fluid circuits including line 735, blood circuits including lines 725 and 730, and waste fluid circuits including line 780 may all be flushed with fluid from the container 740. The details of the blood treatment apparatus and its internal plumbing can vary. Replacement fluid may be transferred from the replacement fluid line 735 or from the blood line 735 to the waste line, for example through a filter, to flush the waste portion of the circuit including the waste line 780. Replacement fluid may circulate through the blood circuit including lines 725 and 730 as indicated to flush the blood circuit, at least a portion of which may be closed as indicated by the arterial and venous lines 730 and 735.

Disposable components, such as the circuit sets of FIGS. 8 and 9 or the batch replacement fluid container 625 alone, or other components that may be used with the embodiments disclosed may be packaged with instructions for preparing infusible replacement fluid. For example, the source fluid 150/250 or a concentrate which may be mixed to make the same (FIGS. 1 and 3) may be supplied with instructions for sterile filtering the fluid as described in the instant specification. Such may constitute packages of consumables or reusable components.

Note that benefits of the filtering method and apparatus discussed above may best be achieved by performing the filtration just prior to treatment, although this is not required. The filtering method may be performed at the treatment site. For example, non-sterile concentrate may be stored at the residence of a patient. The concentrate may be diluted with distilled water in a source fluid container (e.g., 196 of FIG. 1) at the residence and processed as discussed in the instant application. Because the infusible fluid is generated at the treatment site, the need for regulatory-cleared fluids, such as might be obtained from a manufacturer, is not avoided. Cost savings and storage-space economies can thus be realized by the patient. This is particularly important in view of the fact that renal replacement therapies are often administered many times per week and storage and cost of consumables can present a serious problem in a residence or any other facility.

Figure 11:
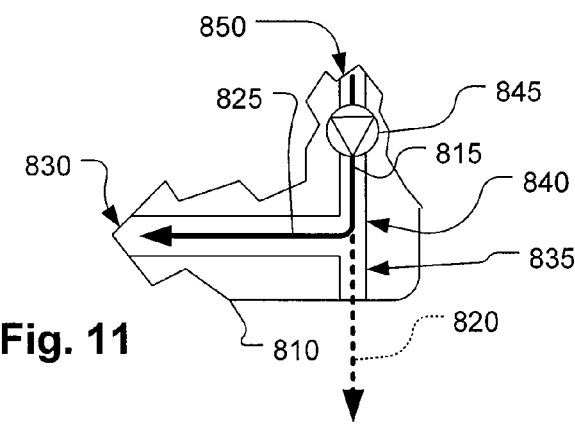
FIG. 11 illustrates a portion of a blood treatment machine that allows a pump used as part of the blood treatment to also be used to control the filtering of fluid to provide a batch of infusible replacement fluid.

Referring now to FIG. 11, a blood treatment machine, a portion of which is illustrated figuratively at 810, may permit a pump 845 that, during treatment, conveys replacement fluid to a patient, to be used for sterile filtering a non-sterile source fluid. Here, the machine 810 has a common guide 850 that accommodates a fluid line 815 through which fluid is conveyed by the pump 845, for example a peristaltic pump. During treatment, the line 815-825 may be guided by a first selected guide 830 in a first direction toward other components of an internal fluid circuit (not shown) as indicated at 825. During sterile-filtering, fluid may be pumped by the same pump 845 through a line 815-820 that is allowed to pass out of the blood treatment machine 810 via a different guide 835. This allows the line 815-820 to be fed to an external connection to the sterile fluid container (not shown) as indicated at 820.

Figure 12:
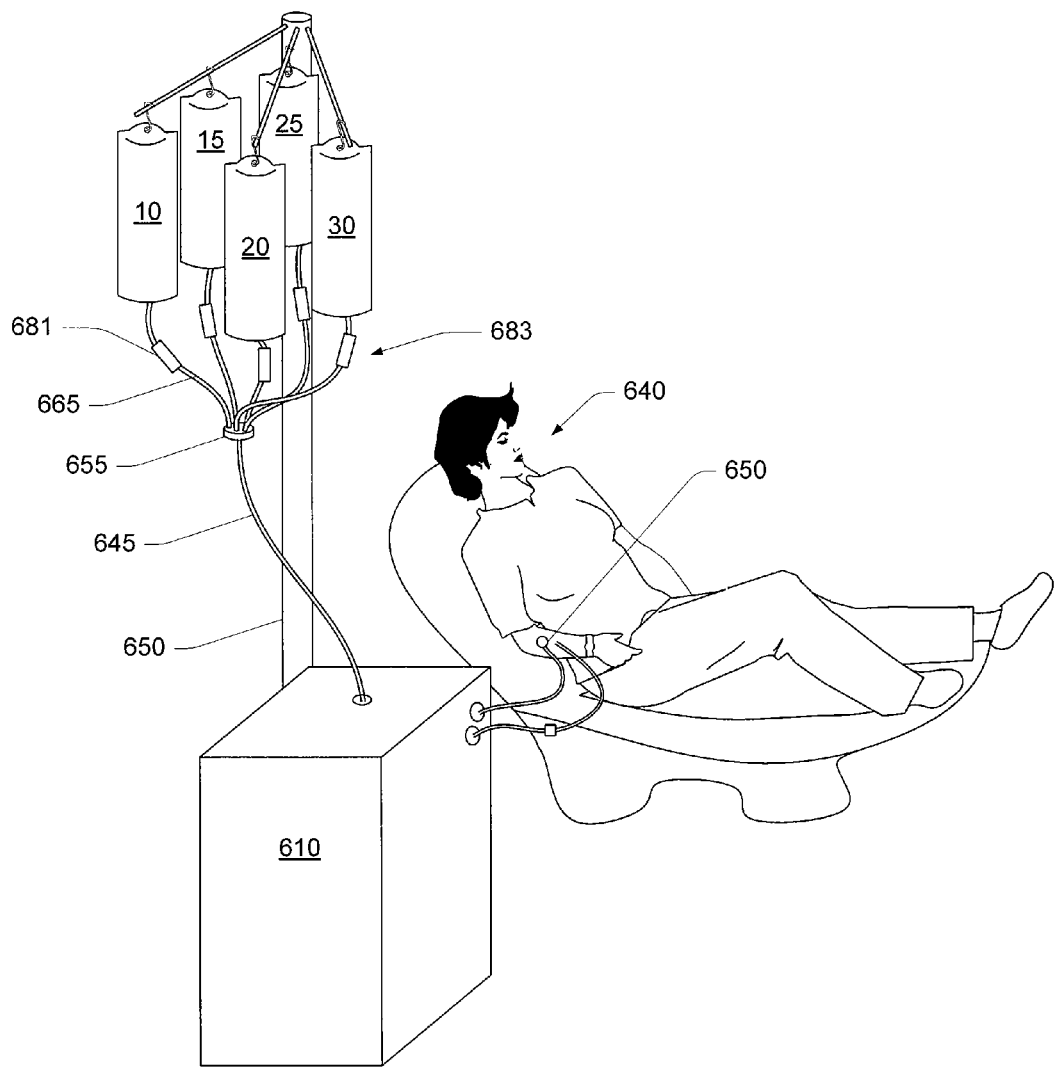
FIG. 12 illustrates a patient undergoing treatment.
Figure 13:
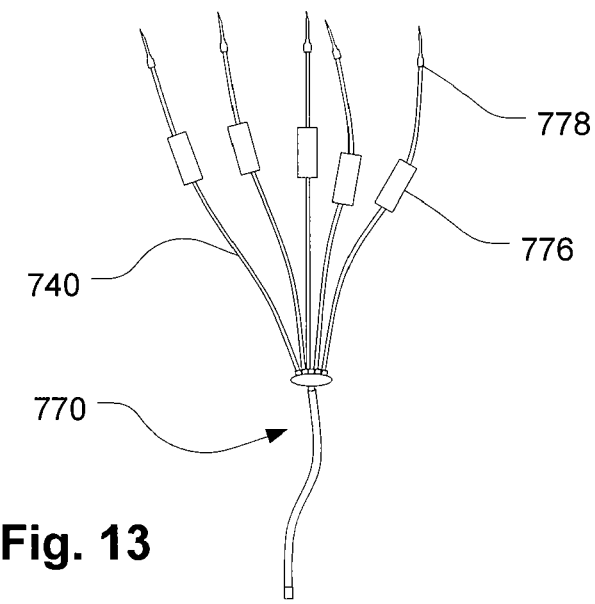
FIGS. 13 and 14 illustrate embodiments of a filtering manifold for filtering of infusible fluids.
Figure 14:
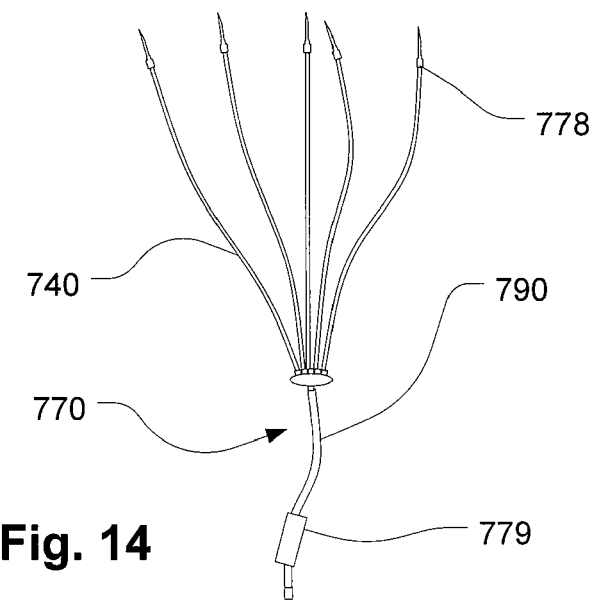

Referring now to FIGS. 12-14, a patient 640 receives a blood treatment by a continuous process performed by a blood treatment machine 610. The process extracts fluid from the blood of the patient 640 which must be replaced to prevent the patient 640 from dehydrating. For example, the treatment process may be hemofiltration or hemodiafiltration. In such processes, blood may be drawn from the patient 640 through an access 650 and returned to the patient 640 through the same access 650.

As is known in the art, the treatment process provided by the blood treatment machine 610 may remove substantial quantities of fluids including electrolytes from the patient's 640 blood. As part of the process, as is also known, fluid may be provided to the patient 640 during treatment. During hemofiltration, for example, multiple liters of fluid may be required to replace what is withdrawn from the patient during treatment. Such fluid may require multiple standard containers 10-30 to make up a sufficient quantity to treat the patient 640.

The desired low levels of endotoxins discussed above may be provided by means of a manifold 683 having inline filters 681 on each arm 665 of the manifold 683. The manifold 683 has a header 655 connecting each arm 665 to a common feed line 645. Referring to FIGS. 13 and 14, filters may be located on each arm 740 of a manifold 770 as indicated at 776 or on a common feed line 790 as indicated at 779. Either embodiment may include spikes 778 or other suitable connectors for connecting to the source containers 10-30. Again, the filters

681, 776, and 779 are preferably configured to ensure levels of endotoxins in the filtered product are lower than 5 EU/Kg./hr. of treatment time and no more than 0.03 EU/ml.

Although the foregoing invention has been described by way of illustration and example, it will be obvious that certain changes and modifications may be practiced that will still fall within the scope of the appended claims. For example, the devices and methods of each embodiment can be combined with or used in any of the other embodiments.

The invention claimed is:

1. A method for supplying sterile fluid to a blood treatment machine, the blood treatment machine consuming said sterile fluid in performing a specified blood treatment on a patient, the fluid being required to be sterile, including an endotoxin level below 0.03 EU/ml, as consumed by the treatment process according to specified requirements of the specified blood treatment, the method comprising:

providing a container of sterile fluid with an endotoxin level below 0.03 EU/ml, the fluid in the container thereby being suitable, without further sterilization, for use by the blood treatment machine in performing the specified blood treatment;

connecting a connector of a fluid line of the blood treatment machine to the container, the connector being such that sterile fluid flowing through the connector is susceptible to contamination by said connecting; and, flowing the sterile fluid from the container through the connector and then through a filter in said fluid line to the blood treatment machine, said filter being effective to remove any contamination generated by said connecting such that in the event of a touch contamination resulting from the connecting, the fluid flowing into the blood treatment machine is restored to an endotoxin level below 0.03 EU/ml.

2. The method of claim 1, wherein the filter is effective to reduce a concentration of endotoxins in the fluid supplied to the blood treatment machine so as to deliver no more than 5 EU/hr per kg of patient weight of fluid upon filtration thereof at a defined rate of infusion into the patient.

3. The method of claim 1, wherein the specified blood treatment includes one of hemofiltration and hemodiafiltration.

4. The method of claim 1, wherein the filter includes a membrane of charged nylon.

5. The method of claim 1, wherein said container comprises a bag of sterile fluid and said connector comprises a spike.

6. A method for supplying sterile fluid to a blood treatment machine that consumes fluid in a process of performing a specified blood treatment, said fluid consumed being required to be sterile, and have a concentration of endotoxins below 0.03 EU/ml, for said specified blood treatment, the method comprising:

providing at least one container, the at least one container containing sterile fluid that does not require further sterilization in order to render it suitable for the specified blood treatment;

manually making a connection between the blood treatment machine and the at least one container such that the sterile fluid flowing from the at least one container is susceptible to touch contamination; and flowing fluid from the at least one container through at least one filter to the blood treatment machine, wherein the at least one filter is adapted to remove the touch contamination, which results from making the connection, from fluid conveyed through the at least one filter, thereby restoring the fluid from the at least one container to a sterile condition including an endotoxin level below 0.03 EU/ml for use in the specified blood treatment.

7. The method of claim 6, wherein the at least one container is at least two containers, and the at least one filter is at least one filter for each of the containers, each filter being connected inline in a respective branch of a fluid line connected to each of said at least two containers, whereby fluid from each container is filtered by its own filter.

8. The method of claim 6, wherein the at least one container is at least two containers, and the at least one filter is a single common filter, a respective branch of a fluid line for each container being connected to an inlet of the common filter, whereby fluid from each container is filtered by the common filter.

9. The method of claim 6, wherein the at least one filter is effective to reduce a concentration of endotoxins in the fluid supplied to the blood treatment machine so as to deliver no more than 5 EU/hr per kg of patient weight of fluid upon filtration thereof at a defined rate of infusion into the patient.

10. The method of claim 6, wherein the specified blood treatment includes one of hemofiltration and hemodiafiltration.

11. The method of claim 6, wherein the at least one filter includes a membrane of charged nylon.

12. A method of performing a specified blood treatment on a patient, the method comprising the steps of:

providing a blood treatment machine that consumes sterile fluid in performing the specified blood treatment on the patient, the sterile fluid being required to have an endotoxin concentration below a specified threshold according to requirements of the specified blood treatment, the blood treatment machine having a fluid line with a connector for receiving sterile fluid;

providing a container of fluid, the fluid in said container having an endotoxin concentration below said specified threshold so as to be sufficiently sterile for use by the blood treatment machine in performing the specified blood treatment without any further sterilization;

providing a filter in the fluid line between the connector and the blood treatment machine;

attaching said connector to the container such that the fluid line connects the container of fluid to the blood treatment machine, the attaching being such that the fluid is susceptible to touch contamination, whereby the endotoxin concentration of the fluid exceeds the specified threshold;

flowing the fluid from the container through the filter to the blood treatment machine; and performing the specified blood treatment on the patient using the blood treatment machine, whereby fluid from the container is consumed by the blood treatment machine, wherein contamination, caused by said attaching, of the fluid flowing to the blood treatment machine from the container is removed by flowing the fluid through the filter such that the fluid consumed by the blood treatment machine is restored to the specified threshold.

13. The method of claim 12, wherein the filter is effective to ensure a concentration of endotoxins in the fluid supplied to the blood treatment machine is below 0.03 EU/ml.

14. The method of claim 12, wherein the filter is effective to reduce a concentration of endotoxins in the fluid supplied to the blood treatment machine so as to deliver no more than 5 EU/hr per kg of patient weight of fluid upon filtration thereof at a defined rate of infusion into the patient.

15. The method of claim 12, wherein the specified blood treatment includes one of hemofiltration and hemodiafiltration.

16. The method of claim 12, wherein said requirements of the specified blood treatment include the sterile fluid having a concentration of endotoxins below 0.03 EU/ml.

* * * * *